United States Patent [19] [11] 4,002,611

Yamamoto et al. [45] Jan. 11, 1977

[54] PREPARATION OF BENZODIAZEPINES

[75] Inventors: Hisao Yamamoto, Nishinomiya; Shigeho Inaba, Takarazuka; Tadashi Okamoto, Ashiya; Toshiyuki Hirohashi, Kobe; Kikuo Ishizumi, Minoo; Michihiro Yamamoto, Takarazuka; Isamu Maruyama, Minoo; Kazuo Mori, Kobe; Tsuyoshi Kobayashi, Minoo, all of Japan

[73] Assignee: Sumitomo Chemical Company, Limited, Osaka, Japan

[22] Filed: Feb. 7, 1969

[21] Appl. No.: 797,663

[30] Foreign Application Priority Data

| | | |
|---|---|---|
| Feb. 13, 1968 | Japan | 43-8951 |
| Mar. 5, 1968 | Japan | 43-14449 |
| Mar. 6, 1968 | Japan | 43-14830 |
| Mar. 12, 1968 | Japan | 43-16332 |
| May 8, 1968 | Japan | 43-31142 |

[52] U.S. Cl. .................... 260/239 BD; 260/326.15

[51] Int. Cl.[2] .................... C07D 243/16

[58] Field of Search ................ 260/239 BD, 326.15

[56] References Cited

UNITED STATES PATENTS

| | | | |
|---|---|---|---|
| 3,030,378 | 4/1962 | Mull | 260/326.15 |
| 3,141,890 | 7/1964 | Reeder et al. | 260/239 |
| 3,625,957 | 12/1971 | Fryer et al. | 260/239 |

FOREIGN PATENTS OR APPLICATIONS

| | | | |
|---|---|---|---|
| 6,801,612 | 7/1968 | Netherlands | 260/239 |

OTHER PUBLICATIONS

Witkop, Ann. Chem., vol. 556, pp. 103–114 (1944).
Mentzer et al., Bull. Soc. Chim., France, pp. 555–561 (1950).
Koelsch, J. Am. Chem. Soc., vol. 66, pp. 1983–1984 (1944).
Fryer et al., J. Het. Chem., vol. 4, pp. 355–359 (1967).
Bell et al., J. Med. Chem., vol. 11, pp. 172–174 (1968).
Smith, The Chemistry of Open–Chain Nitrogen Compounds, vol. 1, (W. A. Benjamin, Inc., New York, 1965), pp. 47–50.
Houben–Weyl, Methoden Der Organischen Chemie, vol. 11/2, (Stuttgart, 1958), pp. 181–182.

*Primary Examiner*—Alton D. Rollins
*Attorney, Agent, or Firm*—Stevens, Davis, Miller & Mosher

[57] ABSTRACT

A 1-alkyl-1,2,4,5-tetrahydro-3H-1,4-benzodiazepine derivative is produced by contacting a 1-aminoethylindole derivative with a suitable oxidizing agent and then reducing the resulting 1-acyl-2,3-dihydro-1H-1,4-benzodiazepine derivative. The starting 1-aminoethylindole derivative is prepared by subjecting a 3-phenylindole derivative to cyanomethylation (or carbamoylemethylation) and then reducing the resulting 1-cyanomethyl- (or 1-carbamoylmethyl)-indole derivative. The 1-acyl-1,2,4,5-tetrahydro-3H-1,4-benzodiazepine derivative is useful as a tranquillizer, muscle-relaxant, etc.

4 Claims, No Drawings

PREPARATION OF BENZODIAZEPINES

This invention relates to a method for producing 1-alkyl-1,2,4,5-tetrahydro-3H-1,4-benzodiazepine derivatives, and salts thereof. More particularly, this invention relates to a method for producing 1-alkyl-1,2,4,5-tetrahydro-3H-1,4-benzodiazepine derivatives, and salts thereof, as represented by the general formula (I),

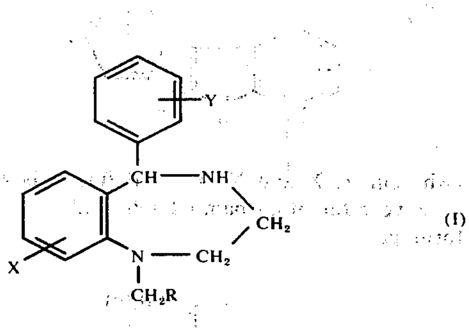

(I)

(wherein R signifies a hydrogen atom or a lower alkyl group, and X and Y signify respectively a hydrogen atom, a halogen atom or a trifluoromethyl group).

In the compounds represented by the general formula (I), halogen atoms represented by X and Y include chlorine, bromine and fluorine, whereas alkyl groups represented by R include a lower alkyl group having one to three carbon atoms such as a methyl, ethyl or propyl group.

1-Alkyl-1,2,4,5-tetrahydro-3H-1,4-benzodiazepine derivatives represented by the aforesaid general formula (I) possess by themselves a tranquillizing, anti-convulsive and muscle-relaxing actions, and moreover are remarkably useful as intermediates in synthesizing other benzodiazepine derivatives which are remarkably effective tranquillizers, anti-convulsants and muscle-relaxants.

Heretofore, the compounds represented by the aforesaid general formula (I) have been produced by reacting an o-aminomethylaniline derivative with an ethylene dihalide such as ethylene dichloride and thereby forming a benzodiazepine ring represented by the following formula (for instance, the Netherland Patent 6,803,742).

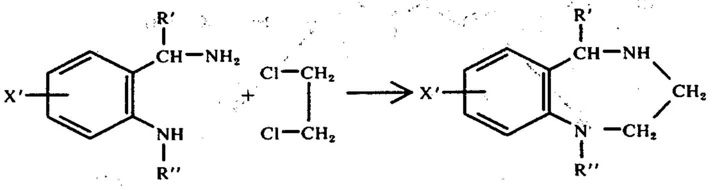

However, this method involves complicated operations, and, for instance, the starting o-aminomethylaniline derivative is not easily obtained.

An object of the present invention is to provide a novel process for preparing benzodiazepine derivatives of the formula (I).

Another object is to provide a novel process for preparing salts of benzodiazepine derivatives by treating the benzodiazepine derivatives of the formula (I) with a mineral acid such as hydrogen chloride, sulfuric or phosphoric acid, or with an organic acid such as maleic, furmaric, succinic, formic, acetic acid or tartaric acid.

Further object of the present invention is to provide novel indole derivatives.

Other objects of the invention will become apparent from the following description.

According to the present invention, a 1-alkyl-1,2,4,5-tetrahydro-3H-1,4-benzodiazepine derivative represented by the general formula (I) is obtained by reducing a 1-acyl-2,3-dihydro-1H-1,4-benzodiazepine derivative represented by the general formula (II),

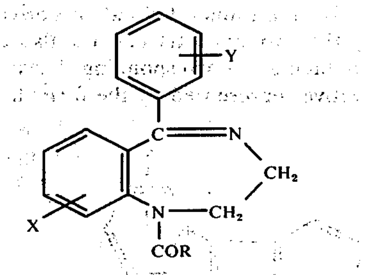

(II)

(wherein R, X and Y are as defined above.)

Further according to the present invention, 1-acyl-2,3-dihydro-1H-1,4-benzodiazepine derivatives of the general formula (II) can be obtained by contacting a 1-aminoethyl-2-(lower alkyl substituted or unsubstituted)-indole derivative, or a salt thereof, represented by the general formula (III), (III)

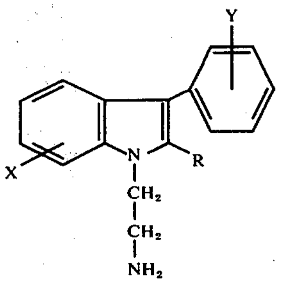

(wherein R, X and Y are as defined above) with an oxidizing agent.

A 1-aminoethyl-indole derivative represented by the aforesaid general formula (III) is a novel compound and can be obtained, for instance, by reducing a corresponding 1-carbamoylmethyl-indole derivative represented by the general formula (IV),

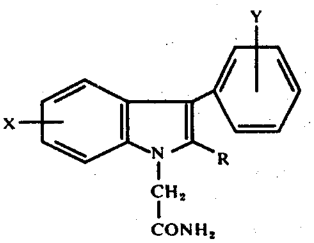
(IV)

(wherein R, X and Y are as defined above.)

Alternatively, a 1-aminoethyl-indole derivative represented by the formula (III) can be also easily obtained by reducing a corresponding 1-cyanomethyl-indole derivative represented by the formula (V),

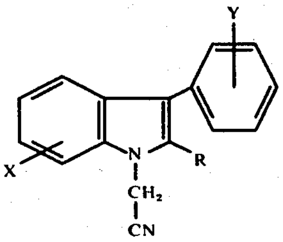
(V)

(wherein R, X and Y are as defined above.)

Both a 1-carbamoylmethyl-indole derivative represented by the general formula (IV) and a 1-cyanomethyl-indole derivative represented by the general formula (V) are novel compounds and the former of the above two compounds can be produced by hydrating the latter compound or also easily produced by reacting an indole derivative represented by the formula (VI),

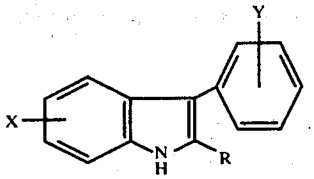
(VI)

(wherein R, X and Y are as defined above.) with a reactive ester of carbamoylmethyl alcohol having the formula

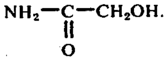

On the other hand, the latter compound represented by the formula (V) can be easily produced by reacting an indole derivative of the formula (VI) and a reactive ester of cyanomethyl alcohol having the formula NC—$CH_2OH$.

Therefore, the process of the present invention is shown by the following synthesis schema:

(VI)

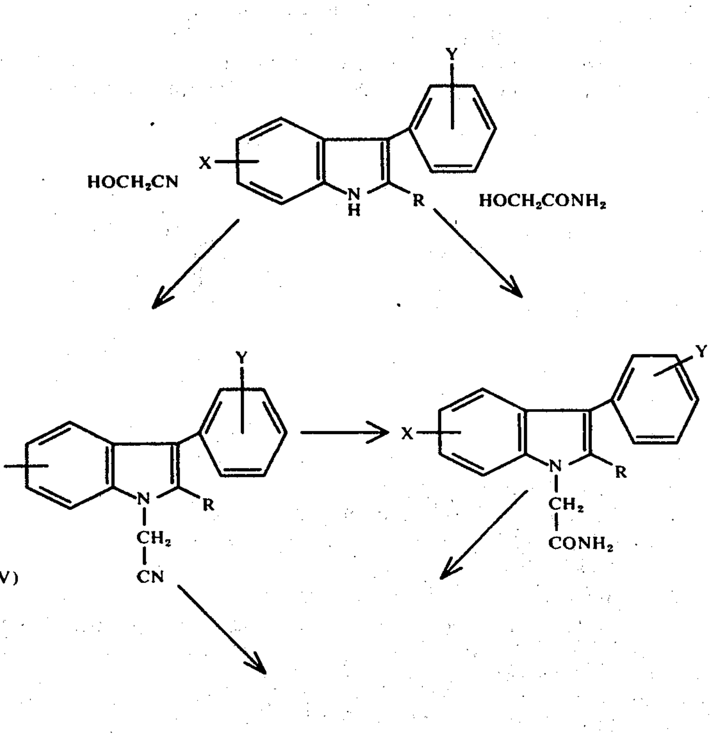

(IV)
(V)

-continued (III)

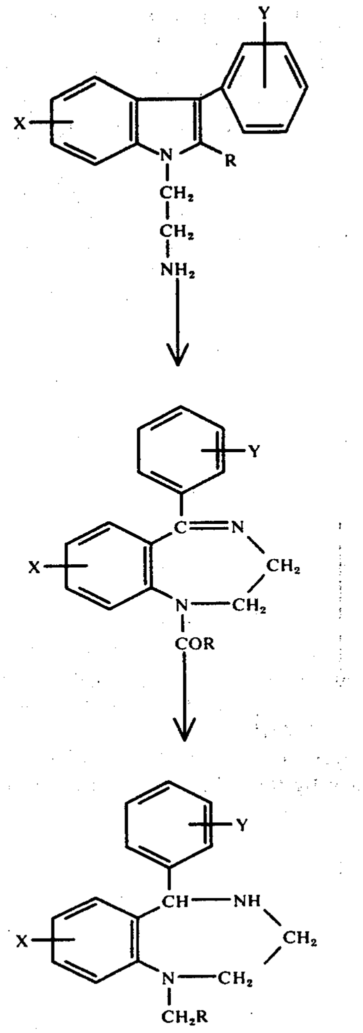

(II)

(I)

All of these processes proceed smoothly and give the objective products in high yields, and therefore these procedures are quite advantageous, in practice.

The indole derivatives of the formula (VI) used as starting materials in this invention are known or may be prepared by the methods reported in the literature, namely, the 3-phenyl-indoles may be prepared by heating phenylacetaldehyde-phenylhydrazones with alcoholic hydrogen chloride, according to E. Fisher and Schmidt, *Ber* 21 1073, 1811 (1888) and the 2-alkyl-3-phenyl-indoles may be prepared by heating methylbenzylketone-phenylhydrazone with alcoholic hydrogen chloride, according to B. Trenkler, *Ann. Chem.* 248 106 (1888).

In the first step of this valuable process, a 1-carbamoylmethyl-indole derivative represented by the formula (IV), (IV)

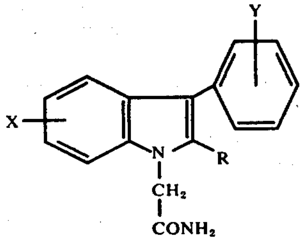

(wherein X, Y and R are as defined above) is obtained by condensing an indole derivative represented by the formula (VI), (VI)

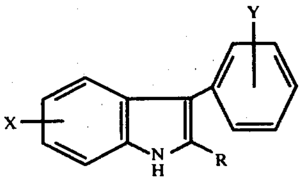

(wherein R, X and Y are as defined above) with a reactive ester of an alcohol represented by the general formula,

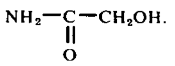

A 1-cyanomethyl-indole derivative which is used in this invention in place of 1-methylcarbamoyl indole derivative and is represented by the formula (V),

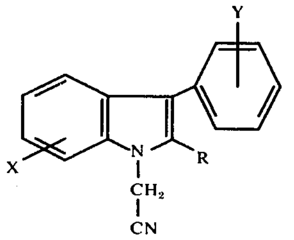

(V)

(wherein R, X and Y are as defined above) can be also obtained by condensing an indole derivative of the formula (VI) with a reactive ester of a cyanomethyl alcohol represented by the formula, $NC—CH_2—OH$.

As mentioned before, the said 1-carbamoylmethyl-indole derivatives of the formula (IV) can be obtained by hydrating the 1-cyanomethyl-indole derivatives of this formula (V).

The reactive esters of carbamoylmethyl alcohol or cyanomethyl alcohol in the present invention are halides and esters of sulfonic acids and the like. Examples of the halides include, for instance, chlorides, bromides and iodides and examples of the esters of sulfonic acids include, esters of methanesulfonic acid, p-toluenesulfonic acid and β-naphthalenesulfonic acid.

The reactions are carried out by treating an indole derivative of the formula (VI) with a reactive ester of either carbamoylmethyl alcohol or cyanomethyl alcohol in the presence of an alkaline agent or after the metal salt has been formed with the alkaline reagent.

Examples of the alkaline agents include, for instance, alkali metal hydrides, alkaline earth metal hydrides, alkali metal hydroxides, alkaline earth metal hydroxides, alkali metal amides, alkaline earth metal amides, alkali metal alkoxides, alkaline earth metal alkoxides, alkyl alkali metals, aryl alkali metals and the like. It is preferable to use, sodium hydrides, lithium hydrides, sodium amides, potassium amides, lithium amides, butyl lithium, phenyl sodium, phenyl lithium and the like.

The reactions are carried out usually in a solvent. Suitable solvents are benzen, toluene, xylene, dimethylformamide, dioxane, liquid ammonia or the like.

According to the present invention, 1-substituted indole derivatives, and the salts thereof, can be obtained, for instance, as follows:

1-Cyanomethyl-3-phenyl-indole,
1-Cyanomethyl-3-phenyl-5-chloro-indole,
1-Cyanomethyl-3-phenyl-5-bromo-indole,
1-Cyanomethyl-3-phenyl-6 (or 4)-chloro-indole,
1-Cyanomethyl-3-phenyl-7-chloro-indole,
1-Cyanomethyl-2-methyl-3-phenyl-indole,
1-Cyanomethyl-2-methyl-3-phenyl-5-chloro-indole,
1-Carbamoylmethyl-3-phenyl-5-chloro-indole,
1-Carbamoylmethyl-2-methyl-3-phenyl-5-chloro-indole,
1-Cyanomethyl-2-ethyl-3-phenyl-5-chloro-indole, and
1-Cyanomethyl-2-propyl-3-phenyl-5-chloro-indole.

1-Cyanomethyl-indole derivative of the formula (V) can be converted to the corresponding 1-carbamoylmethyl-indole derivative of the formula (IV) by contacting it with a base. For this purpose, aqueous solutions of an alkali metal hydroxide such as sodium or potassium hydroxide are preferred. It is preferable to solubilize the 1-cyanomethyl-indole derivative in a suitable water-soluble organic solvent prior to contact with the aqueous base, and for this purpose methanol, ethanol, acetone or methyl ethyl ketone are suitable. The reaction is preferably performed in a range of temperature from room temperature to raised temperature, e.g. at the boiling temperature of the solvent.

According to the methods of this invention, the following 1-carbamoylmethyl-indole derivatives, and the salts thereof, for instance, can be produced:

1-Carbamoylmethyl-3-phenyl-indole,
1-Carbamoylmethyl-3-phenyl-5-chloro-indole,
1-Carbamoylmethyl-3-phenyl-6 (or 4)-chloro-indole,
1-Carbamoylmethyl-2-methyl-3-phenyl-5-chloro-indole,
1-Carbamoylmethyl-3-phenyl-5-bromo-indole,
1-Carbamoylmethyl-2-methyl-3-phenyl-indole,
1-Carbamoylmethyl-3-(o-chloro-phenyl)-5-chloro-indole,
1-Carbamoylmethyl-3-(o-fluoro-phenyl)-5-chloro-indole,
1-Carbamoylmethyl-3-(p-chloro-phenyl)-5-chloro-indole,
1-Carbamoylmethyl-2-methyl-3-(o-fluoro-phenyl)-5-chloro-indole, and
1-Carbamoylmethyl-2-ethyl-3-phenyl-5-chloro-indole.

1-Carbamoylmethyl-indole derivatives and 1-cyanomethyl-indole derivatives of the general formulas (IV) and (V) are easily reduced to 1-aminoethyl-indole derivatives of the formula (III). The reduction is carried out according to electrolytic reduction, reduction with alkali metals in alcohols, catalytic reduction using platinum-, palladium- or nickel-system catalysts, or reduction using metal hydride complexes which include lithium aluminium hydride, boron hydride and their mixture with an acid such as aluminium chloride, ferric chloride, boron trifluoride, hydrogen chloride or the like. Particularly the reduction using lithium aluminium hydride or the mixture of, for example, lithium aluminium hydride and aluminium chloride, sodium borohydride and aluminium chloride, sodium borohydride and boron trifluoride or the like, are preferable in that the operation is simple and the selectivity is favorable.

A 1-aminoethyl-indole derivative (III) obtained by the aforesaid reduction can form a corresponding salt by treating with an acid such as, for example, a mineral acid like hydrochloric acid, hydrobromic acid, sulfuric acid, nitric acid, phosphoric acid, acetic acid or the like or an organic acid.

According to the invention, 1-aminoethyl-indole derivatives, and the salts thereof, can be obtained, for example, as follows:

1-(2'-Aminoethyl)-3-phenyl-indole,
1-(2'-Aminoethyl)-3-phenyl-5-chloro-indole,
1-(2'-Aminoethyl)-3-phenyl-6 (or 4)-chloro-indole,
1-(2'-Aminoethyl)-3-phenyl-7-chloro-indole,
1-(2'-Aminoethyl)-3-phenyl-5-bromo-indole,
1-(2'-Aminoethyl)-3-(o-chlorophenyl)-5-chloro-indole, 1-(2'-Aminoethyl)-3-(o-fluorophenyl)-indole,
1-(2'-Aminoethyl)-3-(o-fluorophenyl)-5-chloro-indole,
1-(2'-Aminoethyl)-3-(p-chlorophenyl)-5-chloro-indole,
1-(2'-Aminoethyl)-3-(p-bromophenyl)-5-chloro-indole,
1-(2'-Aminoethyl)-2-methyl-3-phenyl-indole,
1-(2'-Aminoethyl)-2-methyl-3-phenyl-5-chloro-indole,
1-(2'-Aminoethyl)-2-methyl-3-phenyl-5-bromo-indole,
1-(2'-Aminoethyl)-2-methyl-3-(o-chlorophenyl)-5-chloro-indole,
1-(2'-Aminoethyl)-2-methyl-3-(o-fluorophenyl)-5-chloro-indole,
and their hydrochlorides, hydrobromides and sulfates.

The thus obtained 1-aminoethyl-indole derivatives, or salt thereof, represented by the formula (III) can be converted to a 1-acyl-2,3-dihydro-1H-benzodiazepine derivatives of the formula (II) by contacting with an oxidizing agent.

These 1-acyl-2,3-dihydro-1H-benzodiazepine derivatives possess an anti-convulsive, muscle-relaxing and tranquillizing actions. Furthermore, they are extremely useful as an intermediate for synthesizing 2,3-dihydro-1H-benzodiazepine derivatives which are remarkably effective as an anti-convulsant, muscle-relaxant and tranquillizer.

This oxidation is carried out by contacting a 1-amino-ethyl-indole derivative represented by the aforesaid general formula (III) with a suitable oxidizing agent. The suitable oxidizing agents are ozone, hydrogen peroxide, peracids (for example, peracetic acid, performic acid, perbenzoic acid and the like), chromic acid, permanganates, and the like. The reaction is generally carried out in a solvent. Examples of the suitable solvent include water, chloroform, carbon tetrachloride, acetone, acetic acid, methanol, ethanol, sulfuric acid or others.

Such a process for converting a 5-membered ring compound into a 7-membered ring compound by ring expansion reaction has not heretofore been described or suggested in the literature. This new and useful process thus differs markedly from the known methods and represents an improvement thereover.

According to the process of this invention, for instance, the following compounds, and the salts thereof, can be produced.

1-Formyl-5-phenyl-2,3-dihydro-1H-1,4-benzodiazepine,
1-Formyl-5-phenyl-7-chloro-2,3-dihydro-1H-1,4-benzodiazepine,
1-Formyl-5-phenyl-7-bromo-2,3-dihydro-1H-1,4-benzodiazepine,
1-Formyl-5-phenyl-6 (or 8)-2,3-dihydro-1H-1,4-benzodiazepine,
1-Formyl-5-phenyl-7-trifluoromethyl-2,3-dihydro-1H-1,4-benzodiazepine,
1-Formyl-5-(o-chloro-phenyl)-7-chloro-2,3-dihydro-1H-1,4-benzodiazepine,
1-Formyl-5-(o-fluoro-phenyl)-7-chloro-2,3-dihydro-1H-1,4-benzodiazepine,
1-Acetyl-5-phenyl-2,3-dihydro-1H-1,4-benzodiazepine,
1-Acetyl-5-phenyl-7-chloro-2,3-dihydro-1H-1,4-benzodiazepine,
1-Acetyl-5-phenyl-7-trifluoromethyl-2,3-dihydro-1H-1,4-benzodiazepine,
1-Acetyl-5-(o-fluoro-phenyl)-7-chloro-2,3-dihydro-1H-1,4-benzodiazepine and
1-Propionyl-5-phenyl-7-chloro-1,3-dihydro-1H-1,4-benzodiazepine.

In the final step of this valuable synthetic method, 1-acyl-2,3-dihydro-1H-1,4-benzodiazepine derivative, or salt thereof, represented by the formula (II) is converted to 1-alkyl-1,2,4,5-tetrahydro-3H-1,4-benzodiazepine derivative of the formula (I) by contacting with an appropriate reducing agent. Examples of the appropriate reducing agents in the present process include metal hydride complexes such as lithium aluminium hydride, boron hydride and their mixture with an acid such as aluminium hydride, boron trifluoride or the like.

1-Alkyl-1,2,4,5-tetrahydro-3H-1,4-benzodiazepine derivatives obtained by the above-stated process can form its salts by contacting with an acid, for instance, such inorganic or organic acids as hydrogen chloride, sulfuric acid, phosphoric acid, acetic acid, maleic acid, fumaric acid, succinic acid, tartaric acid and the like.

According to the process of this invention, the following compounds, and the salts thereof, can be produced:

1-Methyl-5-phenyl-1,2,4,5-tetrahydro-3H-1,4-benzodiazepine,
1-Methyl-5-phenyl-7-chloro-1,2,4,5-tetrahydro-3H-1,4-benzodiazepine,
1-Methyl-5-phenyl-7-bromo-1,2,4,5-tetrahydro-3H-1,4-benzodiazepine,
1-Methyl-5-phenyl-6 (or 8)-chloro-1,2,4,5-tetrahydro-3H-1,4-benzodiazepine,
1-Methyl-5-phenyl-7-trifluoromethyl-1,2,4,5-tetrahydro-3H-1,4-benzodiazepine,
1-Methyl-5-(o-chlorophenyl)-7-chloro-1,2,4,5-tetrahydro-3H-1,4-benzodiazepine,
1-Methyl-5-(o-fluorophenyl)-7-chloro-1,2,4,5-tetrahydro-3H-1,4-benzodiazepine,
1-Ethyl-5-phenyl-1,2,4,5-tetrahydro-3H-1,4-benzodiazepine,
1-Ethyl-5-phenyl-7-chloro-1,2,4,5-tetrahydro-3H-1,4-benzodiazepine,
1-(n-Propyl)-5-phenyl-7-chloro-1,2,4,5-tetrahydro-3H-1,4-benzodiazepine and
1-(n-Butyl)-5-phenyl-7-chloro-1,2,4,5-tetrahydro-3H-1,4-benzodiazepine.

The following examples are given for the purpose of illustration and not by way of limitation.

EXAMPLE 1

Preparation of 1-cyanomethyl-3-phenyl-5-chloro-indole:

A solution of 4 g. of 3-phenyl-5-chloro-indole in 10 ml. of dimethylformamide is added dropwise to a suspension of 0.96 g. of 50% sodium hydride (in paraffin) in 10 ml. of dimethylformamide at 25°–30° C.

After the reaction mixture is stirred at a room temperature for 15 minutes, a solution of 1.55 g. of 98% chloroacetonitrile in 10 ml. of dimethylformamide is added dropwise to the mixture at 25° C. Stirring is continued for additional one hour at 25° C.

The resultant mixture is diluted with water and is extracted with ether. The etheral layer is washed with water and dried over sodium sulfate. The solvent is removed to an oily residue, which is triturated in 10 ml. of benzene.

Thereto is added 10 ml. of hexane, and the crystals are collected by filtration to give 2.9 g. of 1-cyanomethyl-3-phenyl-5-chloroindole.

Recrystallization from a mixture solvent of benzene and hexane (1:1) gives light yellow needles having a melting point of 92°–93° C.

By the method mentioned above, following compounds are obtained.

1-Cyanomethyl-3-phenyl-indole,
1-Cyanomethyl-3-phenyl-5-bromo-indole,
1-Cyanomethyl-3-phenyl-6 (or 4)-chloro-indole,
1-Cyanomethyl-3-phenyl-7-chloro-indole,
1-Cyanomethyl-2-methyl-3-phenyl-indole,
1-Cyanomethyl-2-methyl-3-phenyl-5-chloro-indole,
1-Cyanomethyl-2-ethyl-3-phenyl-5-chloro-indole and
1-Cyanomethyl-2-(n-propyl)-3-phenyl-5-chloro-indole.

EXAMPLE 2

Preparation of 1-carbamoylmethyl-3-phenyl-5-chloro-indole:

To a solution of 200 mg. of sodium hydroxide in a solvent mixture of 60 ml. of ethanol and 1 ml. of water is added 2.7 g. of 1-cyanomethyl-3-phenyl-5-chloro-indole and the mixture is refluxed for one hour. After the ethanol is removed under reduced pressure, water is added thereto. After the resultant mixture is extracted with ether, the ethereal layer is washed with water, and dried over sodium sulfate.

Removing the solvent gives 1 g. of yellow brown solid. This solid is recrystallized from ethanol to give 1-carbamoylmethyl-3-phenyl-5-chloro-indole as light yellow brown needles having a melting point of 220°–221° C.

According to the method mentioned above, following compounds are obtained.

1-Carbamoylmethyl-3-phenyl-indole,
1-Carbamoylmethyl-3-phenyl-6 (or 4)-chloro-indole,
1-Carbamoylmethyl-3-phenyl-5-bromo-indole,
1-Carbamoylmethyl-2-methyl-3-phenyl-indole,
1-Carbamoylmethyl-3-(o-chloro-phenyl)-5-chloro-indole,
1-Carbamoylmethyl-3-(o-fluoro-phenyl)-5-chloro-indole,
1-Carbamoylmethyl-3-(p-chloro-phenyl)-5-chloro-indole and
1-Carbamoylmethyl-2-methyl-3-(o-fluoro-phenyl)-5-chloro-indole.

EXAMPLE 3

Preparation of 1-carbamoylmethyl-2-methyl-3-phenyl-5-chloroindole:

A solution of 3 g. of 2-methyl-3-phenyl-5-chloro-indole in a solvent mixture 7 ml. of toluene and 5 ml. of dimethylformamide is added to a suspension of 0.6 g. of 50% sodium hydride (in paraffin) in 5 ml. of toluene at 20° C. After the reaction mixture is stirred at 20° C. for one hour, a solution of 1.1 g. of chloroacetamide in 20 ml. of dimethylformamide is added thereto at 20° C., and the reaction mixture is stirred under reflux for 5 hours. The resultant mixture is diluted with water and is extracted with benzene. The organic layer is washed with water and dried over sodium sulfate. The solvent is removed to a residue, which is recrystallized from ethanol to give 1-carbamoylmethyl-2-methyl-3-phenyl-5-chloroindole, m.p. 223°–224° C.

According to the method mentioned above, following compounds are obtained.

1-Carbamoylmethyl-3-phenyl-5-chloro-indole,
1-Carbamoylmethyl-3-phenyl-indole,
1-Carbamoylmethyl-3-phenyl-5-bromo-indole,
1-Carbamoylmethyl-3-(o-chloro-phenyl)-5-chloro-indole,
1-Carbamoylmethyl-3-(o-fluoro-phenyl)-5-chloro-indole,
1-Carbamoylmethyl-3-(p-chloro-phenyl)-5-chloro-indole,
1-Carbamoylmethyl-2-methyl-3-(o-fluoro-phenyl)-5-chloro-indole and
1-Carbamoylmethyl-2-ethyl-3-phenyl-5-chloro-indole.

EXAMPLE 4

Preparation of 1-(2'-aminoethyl)-3-phenyl-5-chloro-indole hydrochloride:

To a suspension of 0.5 g. of lithium-aluminum hydride in 15 ml. of ether is added a solution of 2.8 g. of 1-cyanomethyl-3-phenyl-5-chloro-indole in 60 ml. of ether at a room temperature under stirring.

After the reaction mixture is stirred for one hour at 20° C., 100 ml. of moist ether and water is successively added thereto very carefully. The ethereal layer is separated by decantation, and washed with water.

To the ethereal layer is added 40 ml. of 3N hydrochloric acid and the mixture is shaken. The crystals produced are collected by filtration, washed with water and dried to give 1.15 g. of 1-(2'-aminoethyl)-3-phenyl-5-chloro-indole hydrochloride.

Recrystallization from ethanol gives colourless leaflets, which are coloured at around 230° C., and decomposed at 270° C.

According to the above mentioned method, following compounds are obtained.

1-(2'-Aminoethyl)-3-phenyl-indole,
1-(2'-Aminoethyl)-3-phenyl-6 (or 4)-chloro-indole,
1-(2'-Aminoethyl)-3-phenyl-7-chloro-indole,
1-(2'-Aminoethyl)-3-phenyl-5-bromo-indole,
1-(2'-Aminoethyl)-3-(o-chlorophenyl)-5-chloro-indole,
1-(2'-Aminoethyl)-3-(o-fluorophenyl)-indole,
1-(2'-Aminoethyl)-3-(o-fluorophenyl)-5-chloro-indole,
1-(2'-Aminoethyl)-3-(p-chlorophenyl)-5-chloro-indole,
1-(2'-Aminoethyl)-3-(p-bromophenyl)-5-chloro-indole,
1-(2'-Aminoethyl)-2-methyl-3-phenyl-indole,
1-(2'-Aminoethyl)-2-methyl-3-phenyl-5-chloro-indole,
1-(2'-Aminoethyl)-2-methyl-3-phenyl-5-bromo-indole,
1-(2'-Aminoethyl)-2-methyl-3-(o-chlorophenyl)-5-chloro-indole,
1-(2'-Aminoethyl)-2-ethyl-3-phenyl-5-chloro-indole,
1-(2'-Aminoethyl)-2-(n-propyl)-3-phenyl-5-chloro-indole,
and their hydrochlorides, hydrobromides and sulfates.

EXAMPLE 5

Preparation of 1-(2'-aminoethyl)-3-phenyl-5-chloroindole hydrochloride:

To a solution of 10 g. of 1-cyanomethyl-3-phenyl-5-chloro-indole in 80 ml. of tetrahydrofuran is added a catalyst which is prepared by heating 50% Raney alloy in an aqueous solution of sodium hydroxide for one hour at 100° C. Two moles of hydrogen is absorbed in the mixture at 18° C. under an atmospheric pressure for 7 hours. After the catalyst is removed by filtration, tetrahydrofuran is removed under a reduced pressure. The residue is dissolved in 100 ml. of ether, to which solution is added 40 ml. of 3N hydrochloric acid. The mixture is shaken, thereby colorless flakes are separated. The crystals are collected by filtration, washed with ether and dried to give 6.7 g. of 1-(2'-aminoethyl)-3-phenyl-5-chloro-indole hydrochloride.

EXAMPLE 6

Preparation of 1-formyl-5-phenyl-7-chloro-2,3-dihydro-1H-1,4-benzodiazepine:

To a suspension of 2.7 g. of 1-(2'-aminoethyl)-3-phenyl-5-chloro-indole hydrochloride in 30 ml. of acetic acid is added a solution of 2.7 g. of chromic anhydride in 3 ml. of water at 10°–15° C. The reaction mixture is stirred for 16 hours at 20° C. The reaction mixture is poured into 500 ml. of water and neutralized to pH 7–8 with ammonia water and extracted with chloroform. The chloroform layer is washed with water and dried over sodium sulfate. The solvent is removed by distillation to an oily residue, to which is added ethanol and insoluble matter is removed by filtration. The filtrate is evaporated to a solidal residue, to which is added isopropanol. After heating, the mixture is cooled to give a light brown insoluble substance, which is removed by filtration. Water is added to the filtrate and the mixture is extracted with 300 ml. of ether, and ethereal layer was washed with water, dried and thereafter the ether is removed by distillation to give a light yellow-white powder. It is recrystallized from a solvent mixture of ethanol and hexane to give 1-formyl-5-phenyl-7-chloro-2,3-dihydro-1H-1,4-benzodiazepine having a melting point of 245° C. (decomp.). And, the crystals are colored around 230° C.

According to the method similar to that of Example 6, the following compounds, can be produced:

1-Formyl-5-phenyl-2,3-dihydro-1H-1,4-benzodiazepine,
1-Formyl-5-phenyl-7-bromo-2,3-dihydro-1H-1,4-benzodiazepine,
1-Formyl-5-phenyl-6 (or 8)-2,3-dihydro-1H-1,4-benzodiazepine,
1-Formyl-5-phenyl-7-trifluoromethyl-2,3-dihydro-1H-1,4-benzodiazepine,
1-Formyl-5-(o-chloro-phenyl)-7-chloro-2,3-dihydro-1H-1,4-benzodiazepine,
1-Formyl-5-(o-fluoro-phenyl)-7-chloro-2,3-dihydro-1H-1,4-benzodiazepine,
1-Acetyl-5-phenyl-2,3-dihydro-1H-1,4-benzodiazepine,
1-Acetyl-5-phenyl-7-chloro-2,3-dihydro-1H-1,4-benzodiazepine,
1-Acetyl-5-phenyl-7-trifluoromethyl-2,3-dihydro-1H-1,4-benzodiazepine,
1-Acetyl-5-(o-fluoro-phenyl)-7-chloro-2,3-dihydro-1H-1,4-benzodiazepine and
1-Propionyl-5-phenyl-7-chloro-1,3-dihydro-1H-1,4-benzodiazepine.

EXAMPLE 7

Preparation of 1-methyl-5-phenyl-7-chloro-1,2,4,5-tetrahydro-3H-1,4-benzodiazepine:

To a suspension of 400 mg. of lithium aluminum hydride in 10 ml. of tetrahydrofuran is added a solution of 600 mg. of 1-formyl-5-phenyl-7-chloro-2,3-dihydro-1H-1,4-benzodiazepine in 40 ml. of tetrahydrofuran at a room temperature. After the reaction mixture is stirred for one hour at 55° C., water is added thereto carefully. The addition of water is stopped when an aluminum compound begin to precipitate on the bottom of the flask, and the precipitate is removed by filtration. The filtrate is concentrated under a reduced pressure to a solidal substance. The solidal substance is recrystallized from a solvent mixture of benzene and n-hexane to give 400 mg. of 1-methyl-5-phenyl-7-chloro-1,2,4,5-tetrahydro-1H-benzodiazepine, melting point 128°–129° C.

According to the method similar to that of Example 7, the following compounds, and the salts thereof, can be produced:

1-Methyl-5-phenyl-1,2,4,5-tetrahydro-3H-1,4-benzodiazepine,
1-Methyl-5-phenyl-7-bromo-1,2,4,5-tetrahydro-3H-1,4-benzodiazepine,
1-Methyl-5-phenyl-6 (or 8)-chloro-1,2,4,5-tetrahydro-3H-1,4-benzodiazepine,
1-Methyl-5-phenyl-7-trifluoromethyl-1,2,4,5-tetrahydro-3H-1,4-benzodiazepine,
1-Methyl-5-(o-chlorophenyl)-7-chloro-1,2,4,5-tetrahydro-3H-1,4-benzodiazepine,
1-Methyl-5-(o-fluorophenyl)-7-chloro-1,2,4,5-tetrahydro-3H-1,4-benzodiazepine,
1-Ethyl-5-phenyl-7-chloro-1,2,4,5-tetrahydro-3H-1,4-benzodiazepine and
1-n-Propyl-5-phenyl-7-chloro-1,2,4,5-tetrahydro-3H-1,4-benzodiazepine.

What is claimed is:

1. A process for preparing 1-alkyl-1,2,4,5-tetrahydro-3H-1,4-benzodiazepine derivatives, and acid-addition salts thereof, represented by the formula,

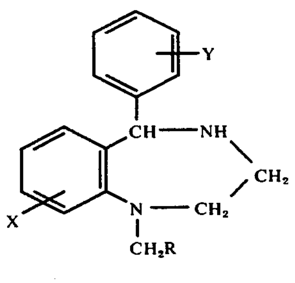

(I)

wherein R signifies a hydrogen atom or an alkyl group having 1 to 3 carbon atoms, and X and Y signify respectively a hydrogen atom, a halogen atom or a trifluoromethyl group; comprising contacting a 1-($C_1$–$C_4$ alkanoyl)-2,3-dihydro-1H-1,4-benzodiazepine derivative, or an acid-addition salt thereof, represented by the formula,

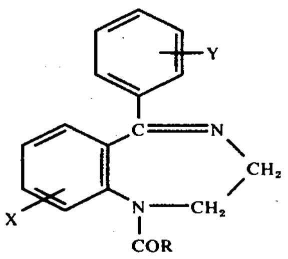

(II)

wherein R, X and Y are as defined above, with a lithium aluminum hydride.

2. A process according to claim 1 wherein the acid of said acid-addition salt is hydrochloric, sulfuric, phosphoric, acetic, maleic, fumaric, succinic or tartaric acid.

3. A process for preparing 1-alkyl-1,2,4,5-tetrahydro-3H-1,4-benzodiazepine derivatives, and acid-addition salts thereof, represented by the formula,

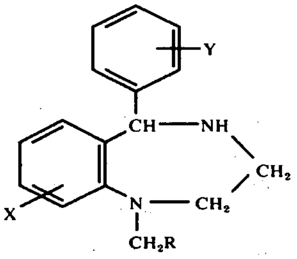

(I)

wherein R signifies a hydrogen atom or an alkyl group having 1 to 3 carbon atoms, and X and Y signify respectively a hydrogen atom, a halogen atom or a trifluoromethyl group; comprising contacting a 1-aminoethyl-indole derivative, or an acid-addition salt thereof, represented by the formula,

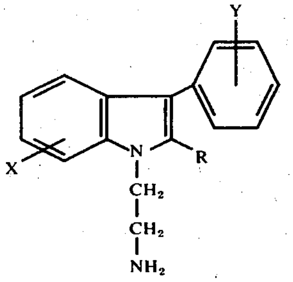

(III)

wherein R, X and Y are as defined above, with an oxidizing agent selected from the group consisting of ozone, hydrogen peroxide, peracids, chromic acid and permanganates, and contacting the resulting 1-($C_1$–$C_4$ alkanoyl)-2,3-dihydro-1H-1,4-benzodiazepine derivative, or an acid addition salt thereof, represented by the formula,

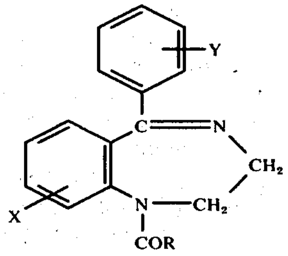

(II)

wherein R, X and Y are as defined above, with a lithium aluminum hydride.

4. A process according to claim 3 wherein the acid of said acid-addition salt is hydrochloric, sulfuric, phosphoric, acetic, maleic, fumaric, succinic or tartaric acid.

* * * * *